United States Patent [19]

Akedo et al.

[11] Patent Number: 4,717,480

[45] Date of Patent: Jan. 5, 1988

[54] METHOD FOR SEPARATION OF LIQUID MIXTURE

[75] Inventors: Takaharu Akedo; Seiichi Manabe, both of Osaka, Japan

[73] Assignee: Agency of Industrial Science and Technology, Tokyo, Japan

[21] Appl. No.: 842,838

[22] Filed: Mar. 24, 1986

[30] Foreign Application Priority Data

May 31, 1985 [JP] Japan .................................. 60-116801
May 31, 1985 [JP] Japan .................................. 60-116802

[51] Int. Cl.$^4$ .............................................. B01D 11/04
[52] U.S. Cl. ..................................... 210/638; 210/650; 210/651; 210/748; 204/181.9; 204/182.3; 204/188; 204/190
[58] Field of Search ............... 210/638, 650, 651, 748; 204/181.9, 182.3, 188, 190

[56] References Cited

U.S. PATENT DOCUMENTS

| | | | |
|---|---|---|---|
| 3,931,000 | 1/1976 | Hamilton | 210/636 |
| 4,203,848 | 5/1980 | Grandine, II | 210/490 |
| 4,265,642 | 5/1981 | Mir et al. | 210/650 |

OTHER PUBLICATIONS

Snyder, D. et al, *A New Electrochemical Process for Treating Spent Emulsions*, General Motors Research Laboratories, GMR-2097, Apr. 9, 1976, pp. 1–28.

Porter, M. C. et al, *Membrane Ultrafiltration*, Chem Tech, Jan. 1971, pp. 56–63.

*Primary Examiner*—Richard V. Fisher
*Assistant Examiner*—Jeffrey W. Peterson
*Attorney, Agent, or Firm*—Birch, Stewart, Kolasch & Birch

[57] ABSTRACT

A method for separation of a liquid mixture wherein a component, intended to be separated, in the liquid mixture is concentrated in the interiors of particles having an average size of 0.1 to 10 μm; the particles are then transported to the surface of a polymeric porous membrane having an average pore size 0.1 to 50 times the average size of the particles under an electrostatic field; and the particles are then separated by a pressure difference loaded on the membrane.

19 Claims, No Drawings

METHOD FOR SEPARATION OF LIQUID MIXTURE

BACKGROUND OF THE INVENTION (1) Field of the Invention

The present invention relates to a method for separating a liquid mixture by using a membrane. More particularly, the present invention relates to a method for separating a liquid mixture, in which an intended component in the liquid mixture is concentrated in the interiors of particles and the particles are then separated by a polymeric porous membrane while transporting the particles under an electrostatic field.

(2) Description of the Related Art

In order to separate a mixture of components having close boiling points or an azeotropic mixture by distillation, it is necessary to repeat distillation several times or carry out azeotropic distillation, and hence, a large quantity of energy is necessary. Reduced pressure distillation or steam distillation is utilized for separating a component which is easily decomposed at a high temperature close to the boiling point. In this case, however, required energy is larger than that in normal pressure distillation. Accordingly, development of a technique of separating a liquid mixture, that can replace the distillation method, is eagerly desired and at the present, a separating method using a membrane attracts attention in the art.

In existing separating techniques using a membrane, a high separating property and a high permeability are not compatible with each other. Namely, if the separating property is high, the permeability is low, or if the permeability is high, the separating property is low. Thus, a separating technique using a membrane, which has a high separating property and a high permeability, has not been developed. Therefore, in the actual operation, the membrane thickness is reduced to increase the permeation of the liquid through the membrane, or the number of the membrane stages is increased to compensate a poor selectivity. However, the former method has a problem in that the strength of the membrane is insufficient, and the latter method has a problem in that the apparatus becomes complicated.

SUMMARY OF THE INVENTION

Under the above-mentioned background, it is the primary object of the present invention to provide a method for separating a liquid mixture by using a polymeric porous membrane wherein a specific component, intended to be separated, can be selectively concentrated from a liquid mixture, for separation of which a large quantity of energy is necessary or the separation of which is difficult, and the rate of permeation per unit area of the membrane can be increased.

We found that the rate of diffusion of molecules in a liquid is 10 to $10^3$ times the rate of diffusion in a solid, that the permeation rate of a polymeric porous membrane to a liquid is high, that the interfaces of particles dispersed in a liquid are electrically charged, that such particles move in a certain direction under an electrostatic field and that the moving speed of the particles is substantially constant irrespective of the particle size. Based on these findings, we have now completed the present invention capable which sufficiently satisfies the above-mentioned desires.

In accordance with the present invention, there is provided a method for separating a liquid mixture, which comprises concentrating a component, intended to be separated, in the interiors of formed particles having an average size of 0.1 to 10 $\mu$m, transporting the particles to the surface of a polymeric porous membrane having an average pore size 0.1 to 50 times the average size of the particles under an electrostatic field and separating the particles by allowing only the particles to pass through the membrane because of a pressure difference loaded on the membrane.

DESCRIPTION OF THE PREFERRED EMBODIMENTS

By the term "liquid mixture" used in the present invention is meant a mixed liquid in which at least two components are present in one homogeneous liquid state under separation operation conditions. The present invention is especially effective for the separation of a mixed liquid containing a liquid having a large latent heat of evaporation, for separation of which a large quantity of energy is necessary according to the distillation method, and a mixed liquid comprising liquids having close boiling points. As examples of such liquid mixtures, there can be mentioned aqueous solutions of alcohols such as methanol, ethanol, n-propanol, isopropanol and t-butanol, aqueous solutions of acetone, methyl ethyl ketone, tetrahydrofuran, dioxane, pyridine and acetic acid, and a methylcyclohexane/toluene liquid mixture and a cyclohexane/toluene liquid mixture. Moreover, the present invention can be applied to the separation of a gas dissolved in a liquid.

A component intended to be separated from a liquid mixture as described above is concentrated in the interiors of particles, and by utilizing surface charges, the particles are transported to the surface of a polymeric porous membrane under an electrostatic field, and only the particle phase is allowed to permeate through the polymeric porous membrane. It is necessary that at the time of this permeation, the average size of the particles should be in a range of from 0.1 to 10 $\mu$m. If the particle size is smaller than 0.1 $\mu$m, because of the Brownian movement of the particles, the transportation of the particles is not efficiently accomplished. If the particle size exceeds 10 $\mu$m, the surface areas of the particles are reduced and the quantity of the mass transfer through the interfaces of the particles becomes small, resulting in reduction of the separating efficiency.

As means to be adopted in the present invention for concentrating the intended component in the interiors of particles from the liquid mixture, there may be adopted a method in which a liquid/liquid phase separating agent or a liquid/liquid extractant is added to the liquid mixture and the mixture is stirred. By the term "liquid/liquid phase separating agent" is meant a substance capable of separating a liquid mixture into a phase containing an intended component in a concentrated state and a phase containing the intended component in a dilute state. As the liquid/liquid phase separating agent, there can be used potassium carbonate for an ethanol/water system, water for a methylcyclohexane/toluene system, ethanol for a cyclohexane/toluene system and toluene for an acetic acid/water system. The intended component moves through the interfaces of the particles and is concentrated in the interiors of the particles.

By the term "liquid/liquid extractant" is meant a liquid which has no mutual solubility with the liquid mixture but is capable of dissolving therein an intended component in a larger amount than the other component of the liquid mixture. A liquid/liquid extractant that can be easily separated from the intended component as the extracted component is preferred. For example, in the case where the liquid mixture is an aqueous solution of an alcohol, a liquid having a water solubility not larger than 0.1 at 30° C. under atmospheric pressure and having a polar group in the chemical structure or a mixed liquid having a water solubility as described above and comprising a liquid having a polar group and a liquid having a water solubility as described above and comprising a liquid having a polar group and a liquid having no polar group, may be used as the liquid/liquid extractant. If the water solubility of the liquid/liquid extractant at 30° C. under atmospheric pressure is larger than 0.1, the liquid/liquid extractant and the aqueous solution of an alcohol as the liquid mixture are partially dissolved in each other, and therefore, particles are not formed and the recovery ratio is reduced at the step of separating particles by the polymeric porous membrane. In view of easy separation of the alcohol from the liquid/liquid extractant, it is preferred that the vapor pressure of the liquid/liquid extractant is not higher than 30 mmHg as measured at 200° C. A pure liquid having in the chemical structure thereof at least one polar group selected from the group consisting of —COO—, —O—, >C—O, >NH, →N, —S—, —CN,

→P═O , →P, —OH and —NHCO— or a liquid mixture comprising this liquid is especially preferred. Trioctyl phosphate or a mixed liquid comprising trioctyl phosphate and 2,6,10,14-tetramethylpentadecane is particularly preferred as the liquid/liquid extract used for separating an alcohol from an aqueous solution thereof in the method of the present invention.

When the intended component is concentrated in the interiors of the particles from the liquid mixture, a liquid containing a compound capable of reversibly forming a complex with the intended component (hereinafter referred to as "carrier") may be used. The carrier is capable of forming a complex selectively only with the intended component in the liquid mixture, and this complex-forming reaction is reversible. If the intended component is recovered from the complex formed by the carrier and the intended component, the carrier is left and the carrier is directly used again for the recovery. As the carrier, there can be used, for example, an acetylene-diol compound such as 1,1,6,6-tetraphenyl-2,4-hexadiyne-1,6-diol or 1,1,4,4-tetraphenyl-2-butyne-1,4-diol for an aqueous solution of a ketone, and a fluorenol compound such as 9(1-propinyl)fluoren-9-ol for an aqueous solution of an alcohol.

By the term "carrier-containing liquid" is meant a liquid containing the carrier dissolved therein at a concentration of at least 0.001 mole/l, which has such a property that the liquid and the liquid mixture are not mutually dissolved in each other. The kind of the liquid is selected so that the selective and reversible complex-forming capacity of the carrier can be maintained. If the carrier is used in the method of the present invention, a separation factor exceeding the value attained under thermodynamic equilibrium conditions can be obtained.

The reason is considered to be that the carrier is locally present in the interfaces of the particles and the rate of inclusion of the intended component into the interiors of the particles is increased, and the particles are separated by the polymeric porous membrane before attainment of the therodynamic equilibrium.

If the carrier concentration in the carrier-containing liquid is less than 0.001 mole/l, the above effect is insufficient and the amount of the intended component included in the particles is small, and hence, the separation efficiency is reduced. Accordingly, it is preferred that the carrier concentration be at least 0.001 mole/l.

Not only mechanical stirring but also ultrasonic vibration may be utilized for stirring for formation of particles. By controlling the amount of the surface active agent added and the time of application of ultrasonic vibration, the particle size can be controlled and large particles having a size of 0.01 to 10 μm can be formed.

By the mass transfer in the interfaces between the particles and the matrix, the intended component is concentrated in the interiors of the thus-formed particles. By providing a potential difference between the membrane surface and the liquid mixture, the surface-charged particles are transported to the surface of the polymeric porous membrane, and simultaneously, by utilizing the pressure difference between both sides of the membrane and the difference of the surface tension between the particles and the matrix phase, the particles are separated from the mixtures of the particles and the matrix by the polymeric porous membrane.

The potential difference acts as a driving force for efficiently transporting the particles to the membrane surface. The potential difference is provided so that in the case where the particles are positively charged, the membrane through which the particles permeate is negatively charged, and in the case where the particles are negatively charged, the membrane is positively charged. If a potential difference is produced between the surface of the membrane and the liquid mixture, the amount of permeation of the particles through the porous membrane can be increased. Use of an ionic surface active agent for formation of the particles is effective for increasing the surface charges of the particles. In view of the efficiency of transportation of the particles, an anionic surface active agent is preferred as the surface active agent, though the reason is unknown. Simultaneously with the movement, coions having the same charge polarity as that of the particles are produced. When the surface active agent used is anionic, the coions are hydroxyl ions, and when the surface active agent is cationic, the subions are hydrogen ions. It is considered that because of the difference of the mobility between hydrogen ions and hydroxyl ions, the anionic surface active agent gives a higher transfer coefficient of the particles than the cationic surface active agent.

In the case where the liquid mixture is an aqueous solution, if the particles are formed by using an ionic surface active agent having an HLB value of at least 8, the separation of the particles by the polymeric porous membrane and the separation of the surface active agent can be simultaneously accomplished. Incidentally, the HLB (hydrophilic lipophylic balance) value is determined according to the method of Davies [2nd Inter. Congress of Surface Activity, 1 (1957)].

An ionic surface active agent having an HLB value of at least 8 forms particles in the form of a stable OW type emulsion. When these particles are filtered through a hydrophobic polymeric porous membrane, only the interior of the particle phase permeates through the membrane while the majority (at least 95%) of the surface active agent forming the interface is not allowed to permeate through the hydrophobic polymeric porous membrane but is left in the matrix phase. When the above particles are filtered through a hydrophilic polymeric porous membrane, only the matrix phase containing the majority of the surface active agent permeates through the membrane. Even particles formed by using an ionic surface active agent having an HLB value smaller than 8 can be separated by a polymeric porous membrane, but in this case, the separation between the surface active agent and the particle phase is substantially impossible.

By utilizing the difference of the surface tension between the particles thus transported to the surface of the membrane and the matrix phase and the pressure difference between both sides of the membrane, the particle phase is separated from the matrix phase by the polymeric porous membrane.

In a preferred embodiment, an aqueous alcohol solution or an aqueous ketone solution is subject to separation under conditions such that the surfaces of the particles are negatively charged and the potential gradient of the electrostatic field is maintained at not larger than 2,000 V/cm.

If the potential gradient of the electrostatic field exceeds 2,000 V/cm, the effect of promoting transportation of the particles is not enhanced (namely, the transportation speed of the particles reaches the highest level), transportation of other ions occur and, thus, the energy efficiency is reduced.

As the polymeric porous membrane, there is used a membrane having an average pore size 0.1 to 50 times the average diameter of the particles, which pore size is at least 0.02 $\mu$m. If the average pore size of the membrane exceeds 50 times the particle size, the separation of the particles is not sufficient. In contrast, if the average pore size of the membrane is smaller than 0.1 time the particle size or smaller than 0.02 $\mu$m, the permeation quantity of the particles per unit hour is reduced. A sharper pore size distribution of the membrane is preferred, and in view of the permeability of the membrane, it is preferred that the porosity of the polymeric porous membrane be at least 40%.

A porous membrane formed of a polymer or copolymer such as polyethylene, polypropylene, polyvinylidene fluoride, polytetrafluoroethylene, polysulfone, polyvinyl chloride, polyamide, polyvinyl alcohol or cellulose is preferably used in the present invention. The polymeric porous membrane may be prepared according to a known process, for example, a process disclosed in U.S. Pat. No. 4,203,848.

In order to separate the particles while transporting them under an electrostatic field, it is preferred that an electroconductive porous membrane having an electroconductivity of at least $10^{-5}$ s·m be used.

According to the large particles phase-separated in an emulsion state and the matrix component and also to the hydrophilic or hydrophobic characteristics of the used polymeric porous membrane, it is decided whether the large particles permeate through the membrane or the matrix permeates through the membrane. The present invention can be carried out in each case. Furthermore, if a hydrophilic membrane and a hydrophobic membrane are used in combination, the separation of the large particles can be accomplished promptly. If the particle phase is an aqueous liquid and the matrix phase is a non-aqueous liquid, when a hydrophilic polymeric porous membrane is used, the particle phase permeates through the membrane, and when a hydrophobic polymeric porous membrane is used, the matrix phase permeates through the membrane. In this case, when a hydrophilic membrane and a hydrophobic membrane are used in combination, the particle phase permeates through the hydrophilic membrane and the matrix phase permeates through a hydrophobic membrane, and the efficiency of the separation of the particles is further increased. In the case where the particle phase is a non-aqueous liquid and the matrix phase is an aqueous liquid, the particle phase permeates through the hydrophobic membrane and the matrix phase permeates through the hydrophilic membrane. By the "hydrophilic polymeric membrane" used herein is meant a membrane having such a property that when a water drop having a diameter smaller than 2 mm is let to fall down on the surface of the membrane at 25° C. under atmospheric pressure, the contact angle between the membrane and the water drop is 0° to 5°. By the "hydrophobic polymeric membrane" is meant a membrane in which the contact angle with water is more than 10°.

The intended component is recovered from the thus-separated phase of the large particles, and since a large quantity of energy is not necessary for this recovery, the distillation method can be adopted for this recovery.

According to the separating method of the present invention, the separation of a liquid mixture, for which a large quantity of energy is necessary if the separation is carried out by the distillation method, can be shifted to the separation of a mixed liquid which can be easily accomplished by the distillation method.

The average pore diameter and porosity of the polymeric porous membrane and the particle size, referred to in the instant specification and claims, are those determined according to the following methods.

(Average Pore Diameter of Polymeric Porous Membrane)

If the number of pores having a radius of r to r+dr per square centimeter of the porous membrane is expressed as N(r)dr N(r) indicates the pore size distribution function, the average pore radius $\bar{r}i$ of degree i is given by the following equation (1):

$$\bar{r}i = \frac{\int_0^\infty r^i N(r) dr}{\int_0^\infty r^{i-1} N(r) dr} \tag{1}$$

An electron microscope photograph of the surface of the polymeric porous membrane is taken by using a scanning electron microscope. The pore size distribution function N(r) is calculated from this photograph according to the known method and is substituted in the equation (1). More specifically, the scanning electron microscope photograph is enlarged to an appropriate size (for example, 20 cm×20 cm) and printed. Twenty test lines (straight lines) are equidistantly drawn on the print. Each test line crosses many pores. With respect to each of the pores crossed by the test lines, the length of the portion of the test line present in the pore is measured, and the frequency distribution function is calculated. Then, N(r) is determined by using the frequency distribution function, for example, according to the method of stereology (see, for example, "Quantitative Morphology" written by Morio Suwa and published by Iwanami Shoten or S. Manabe et al: Polymer Journal, Vol. 17, No. 6, pp. 775-85 (1985)). The average pore diameter is equal to 2 $\bar{r}$.

(Porosity)

The porosity (Pr) is calculated from the measured value of the apparent density ($\rho a$) according to the following equation (2):

$$Pr = (1 - \rho a/\rho p) \times 100 \qquad (2)$$

In the above equation, $\rho p$ represents the density of the material of the porous membrane, and $\rho a$ is calculated from the measured values of the weight W of the porous membrane and the volume V of the porous membrane inclusive of pores according to the formula of $\rho a = M/V$. Pr is expressed in the percentage.

(Particle diameter)

The diffusion coefficient D is determined according to the light quasi-elastic scattering method [see, for example, D. E. Koppel, J. Chem. Phs., 57, 4814 (1972)]. The average particle diameter rd is calculated from this diffusion coefficient D according to the Einstein-Stokes equation of $D = kT/3\pi \eta rd$.

In the above equation, k represents Boltzmann's constant, T represents the absolute temperature of the emulsion, and $\eta$ represents the viscosity coefficient.

The invention will be described by the following examples.

EXAMPLES 1 THROUGH 3

In 100 ml of an aqueous solution containing 20% by volume of ethanol were incorporated 100 ml of trioctyl phosphate and 0.1 g of sodium laurylsulfate, and ultrasonic vibration having a frequency of 28 KHz was applied to the mixture for a predetermined time to form an emulsion in which particles of trioctyl phosphate having a particle diameter shown in Table 1 were dispersed in the aqueous solution of ethanol. The emulsion was filtered under a pressure of 0.01 kg/cm² at a potential gradient of 4.5 V/cm through a polytetra-fluoroethylene porous membrane (Fluoropore supplied by Sumitomo Electric Ind. Ltd. and having a nominal average pore diameter size of 10 μm). The obtained results are shown in Table 1.

When the emulsion was filtered through the polytetra-fluoroethylene porous membrane, only the phase of trioctyl phosphate dispersed in the form of particles permeated through the membrane and the permeated liquid formed a continuous phase.

When the composition of the liquid which had passed through the membrane in Example 2 was analyzed, it was found that the liquid comprised 90% of trioctyl phosphate, 7.2% of ethanol and 2.8% of water.

COMPARATIVE EXAMPLE 1

The procedures of Example 2 were repeated in the same manner except that the potential gradient was changed to zero. The obtained results are shown in Table 1. From Table 1, it is seen that if a potential gradient is provided, the flow rate is prominently increased.

TABLE 1

|  | Average Particle Diameter (μm) | Flow rate (kg/m² · hr) | Separation Factor of Ethanol to Water from Matrix Phase to Particle Phase |
|---|---|---|---|
| Example 1 | 0.3 | 98.0 | 14.7 |
| Example 3 | 5.0 | 94.5 | 14.3 |
| Comparative Example 1 | 2.5 | 68.4 | 14.1 |

COMPARATIVE EXAMPLE 2

An emulsion in which particles having an average particle size of 0.1 μm were dispersed was prepared in the same manner as in Examples 1 through 3. The emulsion was filtered through a Teflon porous membrane having an average pore diameter 100 times the particle diameter under a pressure of 0.01 kg/cm². No filtrate was obtained. If the pressure was increased beyond 0.05 kg/cm², the filtrate was obtained, but trioctyl phosphate was still dispersed in the filtrate in the form of particles.

EXAMPLE 4

The emulsion obtained in Example 2 was filtered under a pressure of 0.01 kg/cm² through a filtering device having regenerated cellulose porous membrane (supplied by Toyo Roshi and having a nominal average pore diameters of 3 μm) arranged at a part of one surface and a polytetrafluoroethylene porous membrane (having an average pore diameter of 10 μm) arranged at a part of the other surface, while providing a potential gradient of 4.5 V/cm so that the polytetrafluoroethylene membrane had a positive polarity. The flow rate to the Teflon membrane was 97 kg/m².hr and the flow rate to the regenerated cellulose membrane was 70 kg/m².hr. The separation factor of ethanol to water from the matrix phase to the particle phase was 14.

As is seen from the foregoing results, if a hydrophilic polymeric porous membrane and a hydrophobic polymeric porous membrane are used in combination, the rate of separating an emulsion into dispersed liquid drops and a dispersing medium can be increased.

EXAMPLE 5

In 100 ml of an aqueous solution containing 20% by volume of ethanol were incorporated 100 ml of a mixed liquid comprising trioctyl phosphate and 2,6,10,14-tetramethylpentadecane at a weight ratio of 2:1 and 0.2 g of sodium laurylsulfate, and ultrasonic vibration having a frequency of 28 KHz was applied to the liquid mixture for 2 minutes to form an emulsion in which particles of the trioctyl phosphate/2,6,10,14-tetramethylpentadecane mixed liquid having an average particle diameter of 0.3 μm were dispersed in the aqueous solution of ethanol. The emulsion was filtered at a potential gradient of 4.5 V/cm under a pressure of 0.01 kg/cm² through a polytetrafluoroethylene porous membrane having a nominal average pore size of 2.0 μm. Only the phase of trioctyl phosphate/2,6,10,14-tetramethylpentadecane dispersed in the form of particles permeated through the membrane at a flow rate of 48 kg/m².hr, and the permeated liquid formed a continuous phase.

When the composition of the permeated liquid was analyzed, it was found that the liquid comprised 60% of trioctyl phosphate, 30% of 2,6,10,14-tetramethylpentadecane, 8.5% of ethanol and 1.5% of water.

When the permeated liquid was subjected to simple distillation at 105° C., an aqueous solution containing 85% by volume of ethanol was obtained.

EXAMPLE 6

In 100 ml of an aqueous solution containing 10% by weight of acetone were incorporated 100 ml of triocytyl phosphate containing 0.01 mole of 1,1,6,6-tetraphenyl-2,4-hexadiyne-1,6-diol and 0.1 g of sodium laurylsulfate, and ultrasonic vibration having a frequency of 28 KHz was applied to the liquid mixture for 1 minute to obtain an emulsion in which particles of trioctyl phosphate having a diameter of 0.7 μm were dispersed in the aqueous solution of acetone. The emulsion was filtered under a pressure of 0.01 kg/cm² at a potential gradient of 35 V/cm through a polytetrafluoro-ethylene porous membrane (Fluoropore supplied by Sumitomo Electric Ind. Ltd. and having a nominal average pore diameter of 10 μm). The obtained results are shown in Table 2.

At the filtration, only the phase of trioctyl phosphate dispersed in the form of particles permeated through the membrane, and the permeating liquid formed a continuous phase. When the composition of the penetrating liquid was analyzed, it was found that the permeated liquid comprised 87% of trioctyl phosphate, 10% of acetone and 3% of water.

COMPARATIVE EXAMPLE 2

The procedures of Example 6 were repeated in the same manner except that 1,1,6,6-tetraphenyl-2,4-hexadiyne-1,6-diol was not used.

The obtained results are shown in Table 2.

From Table 2, it is seen that the separation factor is increased by using a carrier.

COMPARATIVE EXAMPLE 3

The procedures of Example 6 were repeated in the same manner except that the potential gradient was reduced to zero. The obtained results are shown in Table 2.

From Table 2, it is seen that the flow rate is prominently increased by providing a potential gradient.

TABLE 2

|  | Flow Rate (kg/m² · hr) | Separation Factor of Acetone to Water from Matrix Phase to Particle Phase |
| --- | --- | --- |
| Example 6 | 101 | 30.5 |
| Comparative Example 2 | 103 | 5.0 |
| Comparative Example 3 | 21 | 30.5 |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method for the separation of a designated component from a liquid mixture, which comprises:
   concentrating a designated component, which is originally mixed in a liquid mixture, in the interiors of formed particles having an average diameter of 0.1 to 10 μm,
   transporting said formed particles under an electrostatic field to the surface of a polymeric porous membrane which selectively permits only the passage of said formed particles and which has an average pore diameter of from 0.1 to 50 times the average diameter of said formed particles, and
   separating said formed particles from said liquid mixture by the selective passage of said formed particles through said membrane under a membrane pressure placed on said membrane.

2. A method according to claim 1, wherein the liquid mixture is an aqueous alcohol solution or an aqueous ketone solution and wherein the surfaces of the formed particles are negatively charged, and wherein the potential gradient of the electrostatic field is maintained at not larger than 2,000 V/cm.

3. A method according to claim 2, wherein the liquid mixture is an aqueous solution of methanol, ethanol, n-propanol, isopropanol, t-butanol, acetone or methyl ethyl ketone.

4. A method according to claim 1, wherein the polymeric porous membrane is an electroconductive polymeric porous membrane having an electroconductivity of at least $10^{-5}$ s.m.

5. A method according to claim 1, wherein the designated component is concentrated in the interiors of formed particles which are formed by a complex-forming liquid which contains a compound capable of reversibly forming a complex with said designated component.

6. A method of according to claim 5, wherein the liquid mixture is an aqueous alcohol solution or an aqueous ketone solution and wherein the surfaces of the formed particles are negatively charged, and wherein the potential gradient of the electrostatic field is maintained at not larger than 2,000 V/cm.

7. A method according to claim 6, wherein the designated component is concentrated in the interiors of formed particles which are formed by trioctyl phosphate.

8. A method according to claim 6, wherein the designated component is concentrated in the interiors of formed particles which are formed by a trioctyl phosphate/2,6,10,14tetramethylpentadecane mixture.

9. A method according to claim 5, wherein an ionic surface active agent is used for forming the formed particles which are used for transporting the designated component.

10. A method according to claim 5, wherein the polymeric porous membrane is an electroconductive polymeric porous membrane having an electroconductivity of at least $10^{-5}$ s.m.

11. A method according to claim 5, wherein the concentration of the complex-forming liquid is at least 0.001 mole/liter.

12. A method according to claim 5, wherein the complex-forming liquid is 1,1,6,6-tetraphenyl-2,4-hexadiyne-1,6-diol, 1,1,4,4-tetraphenyl-2-butyne-1,4-diol, or 9(1-propinyl) fluoren-9-ol.

13. A method according to claim 1, wherein an ionic surface active agent is used for forming the formed particles which are used for transporting the designated component.

14. A method according to claim 13, wherein the liquid mixture is an aqueous alcohol solution or an aqueous ketone solution and wherein the surfaces of the formed particles are negatively charged, and wherein the potential gradient of the electrostatic field is maintained at not larger than 2,000 V/cm.

15. A method according to claim 13, wherein the polymeric porous membrane is an electroconductive polymeric porous membrane having an electroconductivity of at least $10^{-5}$ s.m.

16. A method according to claim 1, wherein the liquid mixture is an aqueous solution of tetrahydrofuran, an aqueous solution of dioxane, an aqueous solution of pyridine, an aqueous solution of acetic acid, a methylcyclohexane/toluene mixture a cyclohexane/toluene mixture or a gas dissolved in a liquid.

17. A method according to claim 1, wherein the designated component is concentrated in the interiors of formed particles which are formed by a phase separating agent selected from the group consisting of potassium carbonate, water, ethanol, and toluene.

18. A method according to claim 1, wherein the designated component is conentrated in the interior of formed particles which are formed by an extractant agent selected from the group consisting of trioctyl phosphate and a trioctyl phosphate/2,6,10,14-tetramethylenepentadecane mixture.

19. A method according to claim 1, wherein the polymeric porous membrane is polyethylene, polypropylene, polyvinylidene fluoride, polytetrafluoroethylene, polysulfone, polyvinyl chloride, polyamide, polyvinyl alcohol, or cellulose.

* * * * *